(12) United States Patent
Talukder et al.

(10) Patent No.: US 12,083,167 B2
(45) Date of Patent: *Sep. 10, 2024

(54) OVOTRANSFERRIN TREATMENT FOR THE REPRODUCTIVE TRACT

(71) Applicant: Vets Plus, Inc., Menomonie, WI (US)

(72) Inventors: Jamil Talukder, Memphis, TN (US); Abhijit Ray, Salt Lake City, UT (US); Daniel J. DuBourdieu, Limerick, ME (US); Ajay Srivastava, Menomonie, WI (US); Rajiv Lall, Menomonie, WI (US)

(73) Assignee: Vets Plus, Inc., Menomonie, WI (US)

( * ) Notice: Subject to any disclaimer, the term of this patent is extended or adjusted under 35 U.S.C. 154(b) by 642 days.

This patent is subject to a terminal disclaimer.

(21) Appl. No.: 17/146,859

(22) Filed: Jan. 12, 2021

(65) Prior Publication Data

US 2021/0128695 A1 May 6, 2021

Related U.S. Application Data

(63) Continuation of application No. 15/954,074, filed on Apr. 16, 2018, now Pat. No. 10,905,748.

(51) Int. Cl.
| | |
|---|---|
| *A61K 38/40* | (2006.01) |
| *A61K 9/00* | (2006.01) |
| *A61K 31/12* | (2006.01) |
| *A61K 31/722* | (2006.01) |
| *A61K 36/9066* | (2006.01) |
| *A61P 15/00* | (2006.01) |
| *A61P 31/04* | (2006.01) |

(52) U.S. Cl.
CPC .......... *A61K 38/40* (2013.01); *A61K 9/0034* (2013.01); *A61K 31/12* (2013.01); *A61K 31/722* (2013.01); *A61K 36/9066* (2013.01); *A61P 15/00* (2018.01); *A61P 31/04* (2018.01)

(58) Field of Classification Search
None
See application file for complete search history.

(56) References Cited

U.S. PATENT DOCUMENTS

| | | | |
|---|---|---|---|
| 3,903,265 A | 9/1975 | Meisch | |
| 7,341,732 B2 | 3/2008 | Emery et al. | |
| 10,213,490 B2 | 2/2019 | Bromley et al. | |
| 10,905,748 B2* | 2/2021 | Talukder | A61K 36/9066 |
| 2004/0033938 A1* | 2/2004 | Britten | A61K 9/0019 |
| | | | 514/192 |
| 2009/0162402 A1* | 6/2009 | Emery | G01N 33/53 |
| | | | 424/234.1 |
| 2017/0182133 A1 | 6/2017 | Bromley et al. | |

FOREIGN PATENT DOCUMENTS

WO   WO 9308830 A1   5/1993

OTHER PUBLICATIONS

Giansanti et al. (Nutrients, Nov. 2015; 7(11) 9105-9115) (Year: 2015).*
Mandhwani et al. (Vet World, Dec. 2017; 10(12) 1529-1532) (Year: 2017).*
Daetz et al. (Using Chitosan Microparticles to prevent metritis in lactating dairy cows, Sep. 2014). (Year: 2014).*
Ganz, T,, Iron and infection, Int J Hematol. Jan. 2018; 107(1):7-15.
Gkouvatsos, K., Papanikolaou G., Pantopoulos K., Regulation of iron transport and the role of transferrin, Biochim Biophys Acta., Mar. 2012; 1820(3): 188-202.
Giansanti F., Leboffe L., Angelucci F. and Antonini G., The Nutraceutical Properties of Ovotransferrin and Its Potential Utilization as a Functional Food, Nutrients, 2015, 7, 9105-9115.
Mandhwani et al. Insights into bovine endometritis with special reference to phytotherapy, Vet World, 2017, 10(12) p. 1529-1532.
Overton, M. and Fetrwo J., Proceedings of the 2008 Dairy Cattle Reproduction Council Convention, Nov. 7-8, 2008, Omaha, Nebr.
Raafat D., Kristine von Bargen, Albert Hass, and Hans-Georg Sahlahboub & Mohamed Abdel-Daim, Insights into the Mode of Action of Chitosan as an Antibacterial Compound, Applied and Environmental Microbiology, Jun. 2008, p. 3764-3773 vol. 74.
U.S. Appl. No. 15/954,074, Jamil Talukder, filed Apr. 16, 2018.

* cited by examiner

*Primary Examiner* — Melissa S Mercier
(74) *Attorney, Agent, or Firm* — Daniel A. Blasiole; DeWitt LLP

(57) ABSTRACT

A composition and method of maintaining fertility or treating retained placenta, reproductive tract infection, or reproductive tract inflammation in an animal involves administering ovotransferrin to the reproductive tract of the animal. The ovotransferrin administration protects against and treats reproductive tract infection, while protecting against and treating reproductive tract inflammation such as metritis, and thereby maintains fertility in the animal.

17 Claims, 4 Drawing Sheets

Presence of polymorphs in uterine secretions. Uterine secretion was diluted in normal saline and polymorphs were counted using a hemocytomer under a microscope.

| Control | | | Metritis | | | Treated | |
|---|---|---|---|---|---|---|---|
| Mean | SEM | N | Mean | SEM | N | Mean | SEM |
| 4.500 | 0.320 | | 68.000 | 4.200 | | 6.000 | 0.470 |

OVOTRANSFERRIN TREATMENT FOR THE REPRODUCTIVE TRACT

BIBLIOGRAPHY

Complete bibliographical citations to the documents cited herein can be found in the Bibliography, immediately preceding the claims.

FIELD OF THE INVENTION

The present invention relates to use of ovotransferrin as an antimicrobial treatment of the reproductive tract of mammals for reducing reproductive failure resulting from metritis.

BACKGROUND

The first week after the birth of a calf is critical to the continued health of a cow and subsequent reproduction success. An estimated 90% of dairy cows have uterine bacterial contamination in the first week post-partum. Usually these bacteria get removed by the cow within six weeks by natural processes. However, complications such as sustained uterine infection, reproductive tract inflammation, or retained placenta can have a major impact on milk production or subsequent reproduction. Such complications and their effects can occur quite frequently.

The risk of one type of reproductive tract inflammation, metritis, is around 22% in a typical herd. Predisposing factors are dystocia and retained fetal membranes as well as deficiencies in hygiene and metabolic imbalances around parturition. Metritis, which results in an increase in open days (33 days), lower milk yield (typical loss of $83 per cow), and a decrease in pregnancy from a 17.5% normal rate to 13%, is perhaps the most economically important postpartum disorder in dairy cattle, causing high economic losses due to prolonged days open and involuntary culling. Together, these contribute to an average estimated annual cost of about $380 per cow. For a typical 1000-cow herd in 2008, metritis is estimated as costing $79,000 in losses due to milk loss, culling risk, and reproductive changes (Overton 2008).

Metritis is an inflammation of the uterus and is often associated with malodorous watery uterine discharge and high (about 103° F.) fever. Among other factors, infection with a number of infectious microorganisms plays a role in postpartum metritis. Metritis can present clinically or subclinically. Both clinical and subclinical metritis can have effects on milk production and fertility and, therefore, need to be avoided if possible.

For the farmer, there is a dilemma whether or not to treat cows for possible metritis. A variety of treatment therapies are available with varying success rates and varying costs associated with them. Intrauterine antibiotic therapy is one method. One of the most common antibiotics used is oxytetracycline. However, oxytetracycline treatment shows only limited efficacy and results in antibiotic residues appearing in milk. Prostaglandin (PGF) therapy shows some efficacy but is not economical. Iodine infusion is relatively inexpensive but can adversely affect subsequent reproduction. As such, all of these treatments have issues associated with them.

Successful cleansing of the postpartum cow is a major key to subsequent reproductive status and milk production. The lining of the postpartum uterus is in constant contact with fluid and tissue debris. This fluid and tissue debris can lead to growth with a variety of bacteria and other microorganisms. Whether or not infection develops in the uterus depends on the types of bacteria present and the condition of uterus. The uterus acts as an incubator as far as encouraging the rapid growth and increase in bacteria. The multiplication of bacteria is enhanced by sections of placenta that may cling to the uterine lining after calving. These fragments, sometimes small and sometimes quite large, may resist dislodgement by virtue of various cotyledons that have not released themselves. Cotyledons are button-like attachments that serve as the means for supplying nutrients from the mother cow to the fetus within the uterus. Before birth, the cotyledons range from 80 to 120 in number. In typical circumstances, most cotyledons dislodge during parturition. It is only those that do not release that prove troublesome, as they may retain sections of the placenta. When pieces of attached placenta remain in the uterus, they can lead to infections that can result in metritis. This can have a significant impact on the health of the postpartum cow.

Previous methods for removing dead tissue from the uterus of dairy cows have used liquid hydrogen peroxide. See U.S. Pat. No. 3,903,265. Such methods, however, are difficult to perform properly and can be applied only under specific physiological conditions.

SUMMARY OF THE INVENTION

The present invention directed to maintaining fertility or treating retained placenta, reproductive tract infection, or reproductive tract inflammation in an animal by administering ovotransferrin to the reproductive tract of the animal.

In particular, the present invention is directed to a composition for treating and preventing infectious metritis in a mammal comprising components including a therapeutically effective amount of ovotransferrin, wherein the composition is present in a reproductive tract delivery system.

The invention is further directed to a method of treating and protecting a mammal against infectious metritis comprising administering a composition comprising components including a therapeutically effective amount of ovotransferrin.

In one embodiment, the invention provides a method of treating metritis by inhibiting a bacterial infection that causes metritis. This occurs by killing the biofilm-forming bacteria in the uterus with a composition comprising ovotransferrin by itself or with other antimicrobial agents and in combination with anti-inflammatory agents. These active ingredients are provided in liquid infusions or in solid matrixes.

In another embodiment, the invention prevents metritis from occurring in the first place. The administered ovotransferrin or ovotransferrin in combination with other antimicrobial and anti-inflammatory agents cleanses the uterus of a postpartum animal through antimicrobial and anti-inflammatory actions. Through these actions, the animal is able to maintain health of the reproductive tract.

The objects and advantages of the invention will appear more fully from the following detailed description of the preferred embodiment of the invention made in conjunction with the accompanying drawings.

DETAILED DESCRIPTION OF THE INVENTION

Figure 1:
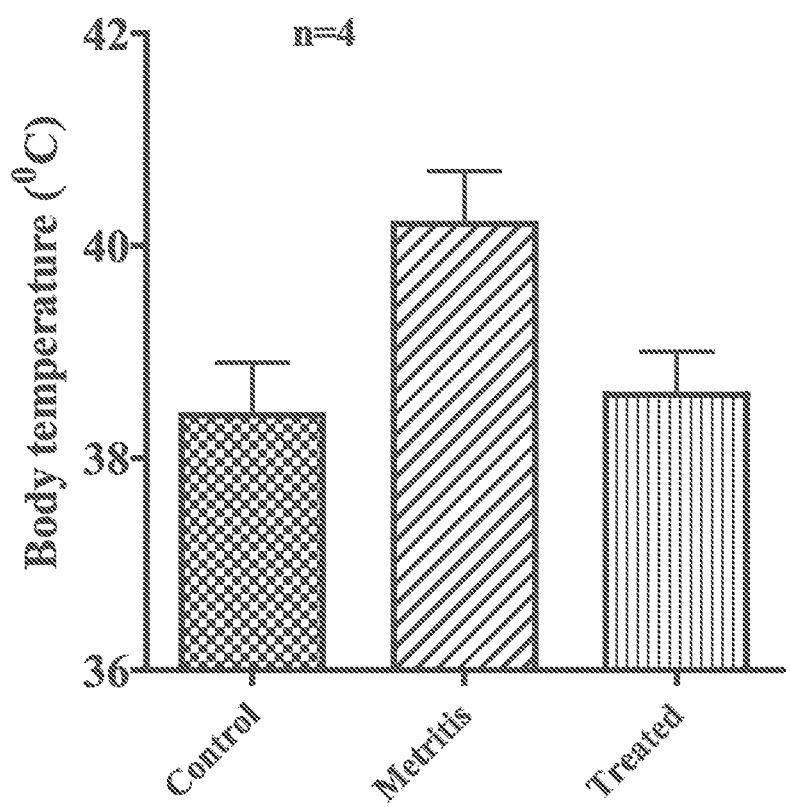
FIG. 1 is a graph illustrating the results of experimentations conducted in Example 2.

The use of the invention provides a method of maintaining animal fertility while maintaining animal productivity. The method comprises administering an effective amount of ovotransferrin to a reproductive tract of an animal. As used herein, "reproductive tract" refers to any of an animal's vulva, vestibule, vagina, cervix, or uterus. For example, ovotransferrin can be administered to any of these parts of the reproductive tract for treatment of infection therein. For uses in maintaining fertility, it is preferred that the ovotransferrin is administered intra-uterally, i.e., in the uterus.

The animal may be suspected of suffering from a retained placenta, reproductive tract infection, or reproductive tract inflammation such as metritis. As used herein, "retained placenta" refers to retention of the placenta, whether the whole placenta or fragments thereof, in the uterus or reproductive tract.

Ovotransferrin:

Transferrins are a group of iron-binding glycoproteins that are responsible for the transport of free iron homeostasis. Several proteins utilize iron as a cofactor for major biological processes. Iron may also catalyze the generation of free radicals thereby promoting oxidative stress. Iron is an essential trace metal for nearly all infectious microorganisms, and host defense mechanisms target this dependence to deprive microbes of iron (Ganz 2018). Transferrins play a major role in acquisition, transport, utilization and storage of iron and are tightly controlled to meet physiological needs and prevent excessive accumulation of the metal within cells (Gkouvatsos 2012).

While in mammals, two different soluble iron-binding glycoproteins are present: (i) serum transferrin and (ii) lactoferrin. In the avian species, the only soluble glycoprotein of the transferrin protein family present is ovotransferrin, present both in avian plasma and egg white and possesses both iron-transfer and protective properties (Giansanti, 2015). Ovotransferrin sequence shares high sequence homology with both human serum transferrin and lactoferrin.

Ovotransferrin, also known as conalbumin, is a protein found in eggs. Twelve to 13% of the total egg white protein is ovotransferrin. Recent evidence indicates that ovotransferrin is endowed not only with the antibacterial activity related to iron withholding, but also with other roles related to the protection of the growing embryo, including: regulation of iron absorption, immune response, and anti-bacterial, anti-viral and anti-inflammatory properties (Giansanti, 2015). It is a member of the transferrin family, a group of ion-binding proteins with an in vivo preference for iron. Ovotransferrin consists of two lobes, each capable of binding one atom of Fe3+ and carbonate anion. Among the two, the N-lobe is found to be more important for its antioxidant properties. Ovotransferrin was reported to possess super oxide dismutase (or SOD)-like activity against superoxide anion promoted by metal binding. The scavenging activity was dose-dependent and considerably higher than known for antioxidants such as ascorbate or serum albumin. Additionally, the iron-binding ability of ovotransferrin has an indirect role in preventing iron-induced lipid peroxidation.

Among the several protective functions of ovotransferrin, the most important one is likely to be the antibacterial activity, which is directly related to the ovotransferrin's ability to bind iron (Fe3+), making it unavailable for bacterial growth. The most sensitive species to the iron deprivation effect of ovotransferrin are *Pseudomonas* spp., *Escherichia coli* and *Streptococcus mutans*, while the most resistant ones are *Proteus* spp., and *Klebsiella* spp. Some studies suggest that part of the antibacterial activity of ovotransferrin is not simply due to the removal of iron from the medium, but also involves more complex mechanisms related to a direct binding of ovotransferrin to the bacterial surface. Ovotransferrin is able to permeate the *E. coli* outer membrane and access the inner membrane, causing both ion leakage inside bacteria and the uncoupling of the respiration-dependent energy production thus killing the bacteria.

Ovotransferrin provides an antiseptic action, likely through the depletion of iron in the macro environment of the infection that kills existing microorganisms and inhibits further microorganism growth within the confines of the reproductive tract. Ovotransferrin also has a more complex mechanism related to a direct binding of ovotransferrin to the bacterial surface. Ovotransferrin is able to permeate the *E. coli* outer membrane and access the inner membrane, causing both ion leakage inside bacteria and the uncoupling of the respiration-dependent energy production thus killing the bacteria. Ovotransferrin is believed to act on the immune cells (T helper cells) that help fight infection. Finally, ovotransferrin has an anti-inflammatory action that helps heal infection. These combined actions effectively treat existing cases of metritis or reduce occurrence of metritis in the postpartum animal. The administered ovotransferrin safely degrades after antimicrobial action and does not harm the animal or the animal's subsequent reproduction. Thus, ovotransferrin administration described herein improves fertility and allows for continued yield of animal products such as milk, with economic gain for the farmer.

Ovotransferrin is preferably present in the composition in an amount sufficient to confer antimicrobial treatment of the reproductive tract of mammals for reducing reproductive failure resulting from metritis. The amount of ovotransferrin included in the composition of the invention can be adapted to the specific needs of the target mammal. As an example, ovotransferrin may be included in an amount of from about 0.1% to about 10.0% w/w, and preferably from about 1.0% to about 5.0% w/w.

Antimicrobial and Anti-Inflammatory Agents

In addition to ovotransferrin, the administered medicament may further include other antimicrobial agents or anti-inflammatory agents. Natural antimicrobial agents such as chitosan or *Curcumin* can be included. Synthetic antimicrobial agents such as cephalosporin, penicillin, macrolides, quinolones, oxazolidinones, aminoglycosides, and sulfonamides can be included in the formulations. Natural anti-inflammatory agents such as phycocyanin, turmeric (*Curcumin longa*) that contains *Curcumin*, garlic (*Allium sativum*), cinnamon (*Cinnamonum* spp.), ginger, (*Zingeber officianale*), Roman chamomile, *Echinacea*, red clover, goldenseal, Vitex (Chaste tree), black pepper, clove can be included in the formulations.

A novel approach of the current invention to prevent or treat mastitis is to combine ovotransferrin with an anti-inflammatory agent. The anti-inflammatory agents can be of an herbal/phytobotanical nature. Certain herbs have been found to be highly beneficial to fight inflammatory conditions as they contain specific compounds that are biologically active. For example, turmeric (*Curcumin longa*) that contains *Curcumin*, garlic (*Allium sativum*), cinnamon (*Cinnamonum* spp.), ginger, (*Zingeber officianale*), Roman chamomile, *Echinacea*, red clover, goldenseal, Vitex (Chaste tree), black pepper, clove are among the phytobotanicals that have known anti-inflammatory activity that can be effective in the invention.

Chitosan

Chitosan is a non-toxic polyglucosamine, widespread in nature, which is deacetylated to varying degrees from chitin, a component of exoskeleton of shrimps, crabs and insects. Because chitosan contains reactive functional groups, e.g., amino acids and hydroxyl groups, it is characterized by antimicrobial, anti-inflammatory, anti-oxidative, antitumor, immunostimulatory and hypocholesterolemic properties when fed as dietary additive for farm animals. Chitosan used as a feed additive for poultry and pigs has some beneficial, biological effects, including immunomodulatory, anti-oxidative, antimicrobial and hypocholesterolemic properties. These properties of chitosan, unlike many other kinds of feed additives, were often reflected in improved growth performance (body weight gain and/or feed conversion ratio) of young animals, that is, broiler chickens and weaned pigs. Chitosan's antimicrobial action, may come from binding of chitosan to teichoic acids in bacteria, coupled with a potential extraction of membrane lipids (predominantly lipoteichoic acid) results in a sequence of events, ultimately leading to bacterial death (Raafat, 2008).

Curcumin

*Curcumin* is the active ingredient of turmeric. It is widely used as a safe kitchen spice and food colorant throughout the world. It is a complex molecule with multiple biological targets and different cellular effects. Its molecular mechanisms of action have been extensively investigated and are known to have anti-inflammatory, antioxidant and anticancer properties. *Curcumin* is a yellow pigment and an active ingredient from turmeric that is typically found in most curry food. The FDA classified turmeric among substances 'generally recognized as safe.' *Curcumin* has been shown to exhibit potent anti-inflammatory and analgesic effects in a variety of experimental animal and human studies. *Curcumin* has been shown to inhibit Cox-2 activity in a number of gastrointestinal cell lines including colon, esophagus and small intestine. Other studies have shown that *Curcumin* is able to inhibit Cox-2 selectively without inhibiting Cox-1 expression.

The anti-inflammatory agent may be included in an amount of from about 0.01% to about 10% w/w of the composition, such as from about 0.1% to about 5% w/w or from about 0.5% to about 1.5% w/w.

Amounts of Components

The amounts of each of the components in the final product may be varied depending upon the nature of the dried proteins, the weight and condition of the animal to be treated, and the unit dosage desired. Those of ordinary skill in the art will be able to adjust dosage amounts as required.

Ratios of the individual components on a weight to weight basis can be 1:1:1 for the ovotransferrin:chitosan:*Curcumin*. Other ratios can be applied, depending on the desired antimicrobial:anti-inflammatory activity required in different circumstances.

Methods of Manufacture or Preparation:

The ingredients of the invention are manufactured from methods known to the art and are commercially available. The ingredients are sourced as dried powders that are mixed together to form the basis of the invention.

Bulking agents can be added as required to make weighing and use of the invention more practical in different situations on the farm. Bulking agents can include commonly used materials approved by the Association of American Feed Control Officials such as cellulose, ethyl cellulose, microcrystalline celluloses, wheat bran, silicon dioxide, Verxite or flours such as from rice, corn or wheat.

In one version, the dried purified preparations of ovotransferrin are added in 200 ml water at a rate of 5% ovotransferrin to create a suspension. This liquid suspension is placed in a hand held low pressurized holding tank.

Delivery (Treatment) of Animal:

The invention is metered out and delivered in a defined dose by connecting tube with nozzle that is inserted into the reproductive tract, and specifically the uterus, of the postpartum animal such as a cow. Alternative delivery systems of the invention include placing the suspension in a syringe system that is connected to tubing that is inserted in the uterus and defined amounts of the invention are delivered. The infusion can be delivered in a suspension having a pH from about 7.5 to about 1.0, preferably from pH 3.5 to pH 2.0. The volume infused, per dose, ranges from about 1 to about 300 ml.

Ovotransferrin may also be delivered in a solid matrix. This is done by mixing ovotransferrin with inert dissolvable binding agents to create a bolus by methods known in the art. The bolus is inserted into the uterus of animals such as cows post parturition to prevent the onset of infection. The ovotransferrin in the bolus is can be administered in an amount of from about 0.001 g per Kg of body weight of the animal to about 0.01 g per Kg body weight of the animal.

Preferred discrete doses include about 1 g or 20 g of ovotransferrin which depends on its use in ovine, caprine, or swine, bovine or equine. The ovotransferrin is preferably administered in one and only one discrete dose. The concentration of ovotransferrin a solid bolus ranges from about 1 to about 30 g, preferably 2.5 to about 14 g. The preferred formulation of the medicament is a bolus including about 2.5 g ovotransferrin per bolus. Such a bolus can be administered directly in whole or in part or can be dissolved in a solvent to generate a flush for administration.

Besides using liquids or solid boluses as a delivery system, other formats can be used. The medicament may comprise a bolus, a liquid flush, a loose powder, a hard-shelled capsule, a soft-shelled capsule, a gel, or a paste.

Types of Animals:

In a preferred version of the invention, the animal is postpartum. Mammals that may be administered the invention include farm animals such as bovine, ovine, caprine, equine, and swine. It can include companion animals such as dogs and cats. It can include zoo animals such as camels, deer and buffalo.

EXAMPLES

Example 1

A cow that was diagnosed with metritis, as evidenced by elevated temperature, elevated total leukocyte count, raised tails, and foul smelling discharge, had the discharge cultured onto blood agar plates. Bacteria colonies with different morphology from the metritis discharge that grew were selected and placed into 20 ml liquid nutrient broth in culture tubes at a defined amount and incubated overnight at 37° C. The bacteria in the liquid nutrient broth was then used to create agar plates by mixing 1 ml of nutrient broth containing bacteria with 15 ml of warm agar and poured into petri dishes and incubated for 24-48 hrs. at 37° C. Then, holes were punched into the agar and a dose response of previously purified ovotransferrin at 0%, 10% and 25% w/v in sterile water was placed in the holes. The plates were allowed to diffuse for 24 hour at 37° C. to check for zone of inhibition. Zones of inhibition were visualized by clearings in the agar where no bacteria grew. Results indicated that a zone of inhibition was seen at 10% wells and a larger zone at the 25% wells. This is consistent with ovotransferrin in killing the bacteria that cause metritis. It was concluded that ovotransferrin of the invention is able to inhibit growth of the metritis causing bacteria in a dose dependent manner.

Example 2

Cows with clinical endometritis (n=4) were identified based on the clinical signs, rectal temperature, score of mucus characteristics, total polymorph numbers, pH of uterine discharge, uterine swab analysis, and bacterial culture, along with healthy cows (control, n=4). Two hundred ml of a 5% ovotransferrin solution of the invention were infused intrauterine with a special pipette attached to a pump in the treatment group. Seven days later, all the above parameters were reexamined. Total number of polymorph in uterine discharge was counted using a hemocytometer, stained with Giemsa and Gram stain.

Results: Rectal temperature were higher at >40° C. in cows with endometritis and was found to be normal (38.5° C.) after one week after treatment with the ovotransferrin of the invention in a liquid infusion format as illustrated in FIG. 1. This indicates the invention is efficacious in treating metritis in cows.

Example 3

Cows with clinical endometritis (n=3) were identified based on the clinical signs, rectal temperature, score of mucus characteristics, total polymorph numbers, pH of uterine discharge, uterine swab analysis, and bacterial culture, along with healthy cows (control, n=3. Two hundred ml of a 5% ovotransferrin solution of the invention were infused intrauterine with a special pipette attached to a pump in the treatment group. Seven days later, all the above parameters were reexamined.

Figure 2:
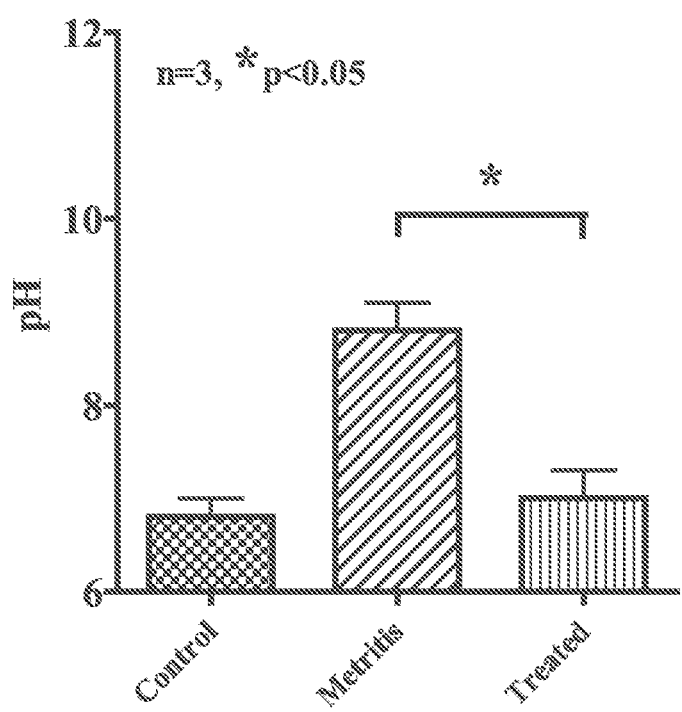
FIG. 2 is a graph illustrating the results of experimentations conducted in Example 3.

Mean pH of uterine discharge from metritis cows was 8.8 (control 6.8) and changed to 7.0 after one week of treatment with the invention in a liquid format. As illustrated in FIG. 2, the results were statistically significant with p<0.05 between the pre and post treatment. This indicates the invention was efficacious for treatment of metritis in cows.

Example 4

Figure 3:
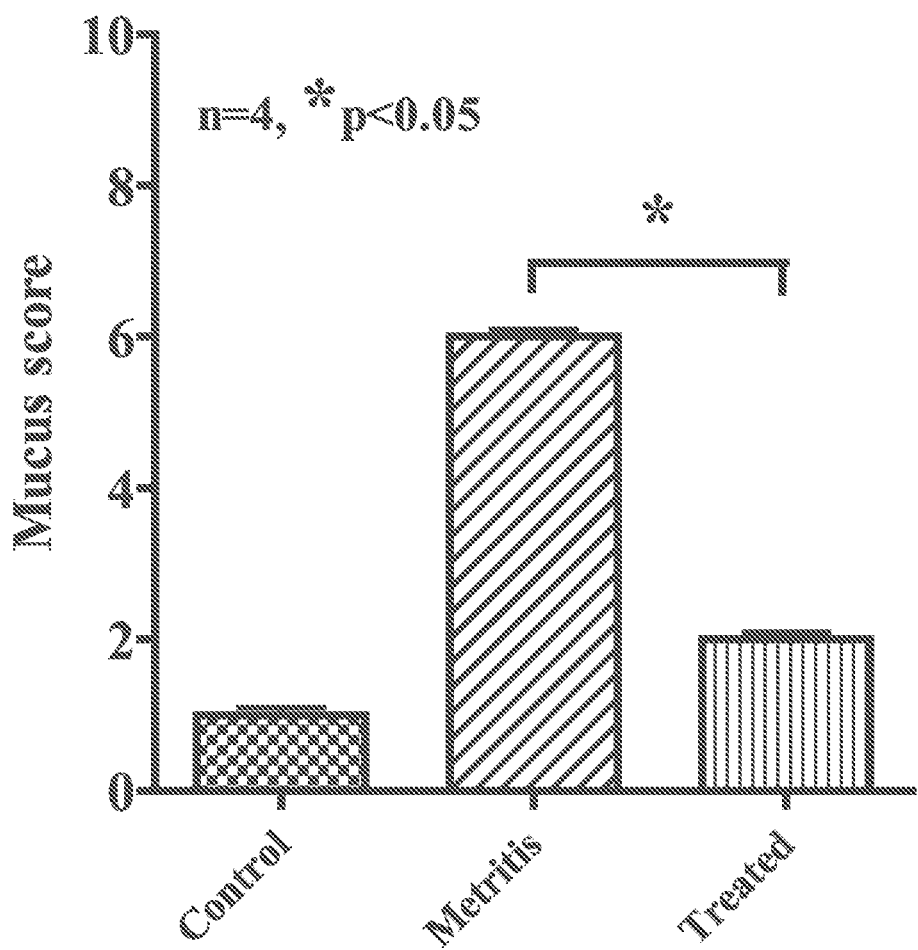
FIG. 3 is a graph illustrating the results of experimentations conducted in Example 4.

Cows with clinical endometritis (n=4) were identified based on the clinical signs, rectal temperature, score of mucus characteristics, total polymorph numbers, pH of uterine discharge, uterine swab analysis, and bacterial culture, along with healthy cows (control, n=4). Two hundred ml of a 5% ovotransferrin solution of the invention were infused intrauterine with a special pipette attached to a pump in the treatment group. Seven days later, all the above parameters were reexamined. Mucus score was 6 times higher in metritis affected cows than control values. After treatment with the liquid format of the invention a statistically significant decrease in the mucus scored occurred in cows that had metritis and was near normal control values, as illustrated in FIG. 3. This indicates the invention was efficacious for treatment metritis in cows.

Example 5

Figure 4:
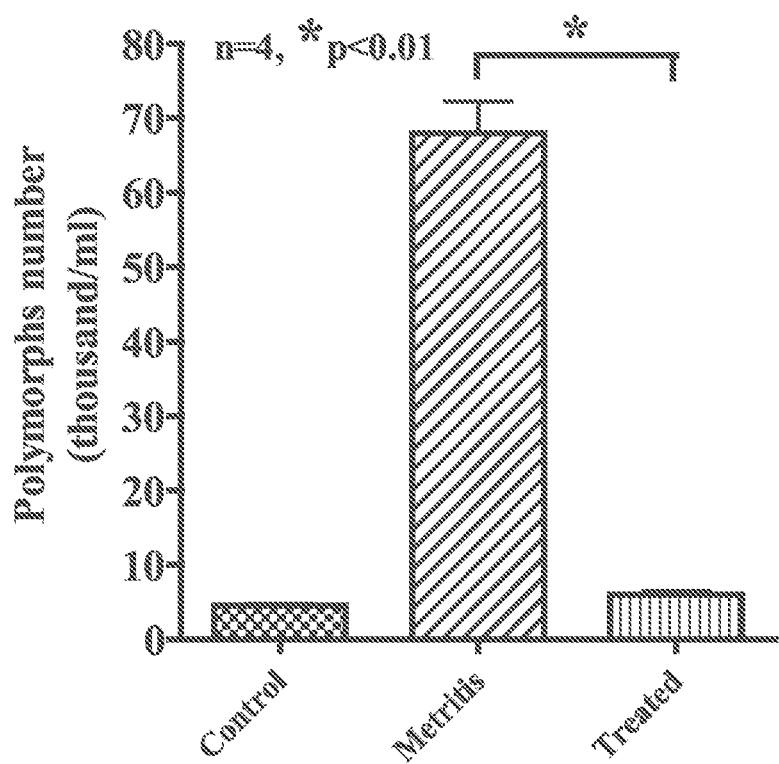
FIG. 4 is a graph illustrating the results of experimentations conducted in Example 5.

Cows with clinical endometritis (n=4) were identified based on the clinical signs, rectal temperature, score of mucus characteristics, total polymorph numbers, pH of uterine discharge, uterine swab analysis, and bacterial culture, along with healthy cows (control, n=4). Two hundred ml of a 5% ovotransferrin solution of the invention were infused intrauterine with a special pipette attached to a pump in the treatment group. Seven days later, all the above parameters were reexamined. Total number of polymorph was more than 70 times higher in cows with metritis and statistically significantly (p<0.01) reduced (2 and 4 times higher, respectively, compared with control) after treatment with the invention in liquid format, as illustrated in FIG. 4. This indicates that the liquid format of the invention is efficacious in treatment of cows with metritis.

Example 6

A clinical trial was conducted to examine efficacy of the invention to prevent infectious metritis in cows. 10 gram of purified Ovotransferrin was mixed with 10 grams of binding agent to create a 20 gram total bolus with dimensions of 2 cm wide and 6 cm long. For N=5 cows from a herd known to have the standard metritis rate were selected that were 3 hours postpartum. Two boluses were inserted into the uterus and allowed to dissolve. The cows were monitor daily for any obvious signs of metritis. After 30 days, the cows were examined in detail for clinical signs of metritis. None of the cows had any signs of metritis. It would be expected that at least one of the cows of this group would have had metritis 10-12 days without the use of the invention. These results are consistent with 20 grams of ovotransferrin in the bolus format of the invention in preventing metritis.

Example 7

A clinical trial was conducted to examine efficacy of the invention to prevent infectious metritis in cows. 10 gram of purified Ovotransferrin was mixed with 10 grams of binding agent to create a 20 gram total bolus with dimensions of 2 cm wide and 6 cm long. For N=5 cows from a herd known to have the standard metritis rate were selected that were 3 hours postpartum. A single bolus was inserted into the uterus and allowed to dissolve. The cows were monitor daily for any obvious signs of metritis. After 30 days, the cows were examined in detail for clinical signs of metritis. None of the cows had any signs of metritis. It would be expected that at least one of the cows of this group would have had metritis 10-12 days without the use of the invention. These results are consistent with 10 grams ovotransferrin in the bolus format of the invention in preventing metritis.

Example 8

A clinical trial was conducted to examine efficacy of the invention to prevent infectious metritis in cows. 2.5 gram of purified Ovotransferrin was mixed with 17.5 grams of binding agent to create a 20 gram total bolus with dimensions of 2 cm wide and 6 cm long. For N=7 cows from a herd known to have the standard metritis rate were selected that were 3 hours postpartum. Two boluses were inserted into the uterus and allowed to dissolve. The cows were monitor daily for any obvious signs of metritis. After 30 days, the cows were examined in detail for clinical signs of metritis. None of the cows had any signs of metritis. It would be expected that at least one of the cows of this group would have had metritis 10-12 days without the use of the invention. These results are consistent with 5 grams ovotransferrin in the bolus format of the invention in preventing metritis.

Example 9

A clinical trial was conducted to examine efficacy of the invention to prevent infectious metritis in cows. 2.5 gram of purified Ovotransferrin was mixed with 17.5 grams of binding agent to create a 20 gram total bolus with dimensions of 2 cm wide and 6 cm long. For N=7 cows from a herd known to have the standard metritis rate were selected that were 3 hours postpartum. A single bolus was inserted into the uterus and allowed to dissolve. The cows were monitor daily for any obvious signs of metritis. After 30 days, the cows were examined in detail for clinical signs of metritis. None of the cows had any signs of metritis. It would be expected that at least one of the cows of this group would have had metritis 10-12 days without the use of the invention. These results are consistent with 2.5 grams.

There are several variations which can be practiced in the scope of this invention. The invention may include a variety of other additives such as additional antimicrobials and anti-inflammatory agents. These may be delivered in different formats.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Ganz, T., "Iron and infection," Int J Hematol. 2018 January; 107(1):7-15.

Gkouvatsos K., Papanikolaou G., Pantopoulos K., "Regulation of iron transport and the role of transferrin," Biochim Biophys Acta., 2012 March; 1820(3):188-202.

Giansanti F., Leboffe L., Angelucci F. and Antonini G., "The Nutraceutical Properties of Ovotransferrin and Its Potential Utilization as a Functional Food," Nutrients, 2015, 7, 9105-9115

Overton, M. and Fetrow J., "Proceedings of the 2008 Dairy Cattle Reproduction Council Convention," Nov. 7-8, 2008, Omaha, Nebr.

Raafat D., Kristine von Bargen, Albert Haas, and Hans-Georg Sahlahboub & Mohamed Abdel-Daim., "Insights into the Mode of Action of Chitosan as an Antibacterial Compound," Applied and Environmental Microbiology, June 2008, p. 3764-3773 Vol. 74.

What is claimed is:

1. A method of treating and protecting a mammal against infectious metritis comprising administering a composition comprising components including a therapeutically effective amount of ovotransferrin.

2. The method of claim 1 wherein the concentration of ovotransferrin in the composition is between 0.1% w/w and 10.0% w/w.

3. The method of claim 1 wherein the concentration of ovotransferrin in the composition is between 1.0% w/w and 5.0% w/w.

4. The method of claim 1 further comprising a therapeutically effective amount of an antimicrobial agent selected from the group consisting of chitosan and Curcumin.

5. The method of claim 1 further comprising a therapeutically effective amount of an antimicrobial agent selected from the group consisting of cephalosporin, penicillin, macrolides, quinolones, oxazolidinones, aminoglycosides, and sulfonamides.

6. The method of claim 1 further comprising a therapeutically effective amount of an anti-inflammatory agent.

7. The method of claim 1 wherein the composition further comprises chitosan and Curcumin.

8. The method of claim 6, wherein the anti-inflammatory agent is selected from the group consisting of garlic, cinnamon, ginger, Roman chamomile, Echinacea, red clover, goldenseal, Vitex, black pepper and clove.

9. The method of claim 6 wherein the anti-inflammatory agent is turmeric containing Curcumin.

10. The method of claim 1 wherein the composition is administered in the reproductive tract of the mammal.

11. The method of claim 1 wherein the composition is administered in an infusion having a pH from about 7.5 to about 1.0.

12. The method of claim 1 wherein the administering comprises inserting the composition in the form of a solid bolus into the reproductive tract of the mammal.

13. The method of claim 12 wherein the solid bolus comprises the ovotransferrin in an amount from about 1 g to about 30 g.

14. The method of claim 12 wherein the solid bolus comprises the ovotransferrin in an amount from about 1 g to about 14 g.

15. The method of claim 1 wherein the administering comprises:
    dissolving a solid bolus comprising the ovotransferrin in a solvent to generate the composition in the form of a liquid; and
    administering the liquid into the uterus of the mammal.

16. The method of claim 15, wherein the solid bolus comprises the ovotransferrin in an amount from about 1 g to about 30 g.

17. The method of claim 15 wherein the solid bolus comprises the ovotransferrin in an amount from about 1 g to about 14 g.

* * * * *